United States Patent
Haggerty (10) Patent No.: US 11,585,646 B2
(45) Date of Patent: Feb. 21, 2023

(54) SHAPED CHARGE EFFECT MEASUREMENT

(71) Applicant: Halliburton Energy Services, Inc., Houston, TX (US)

(72) Inventor: Dennis J. Haggerty, Burleson, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 823 days.

(21) Appl. No.: 16/489,322

(22) PCT Filed: Nov. 27, 2018

(86) PCT No.: PCT/US2018/062630
§ 371 (c)(1),
(2) Date: Aug. 27, 2019

(87) PCT Pub. No.: WO2020/112089
PCT Pub. Date: Jun. 4, 2020

(65) Prior Publication Data
US 2021/0072008 A1 Mar. 11, 2021

(51) Int. Cl.
*E21B 49/02* (2006.01)
*G01N 3/313* (2006.01)
(Continued)

(52) U.S. Cl.
CPC .............. *F42B 35/00* (2013.01); *E21B 49/02* (2013.01); *G01N 3/313* (2013.01);
(Continued)

(58) Field of Classification Search
CPC .... G01N 3/313; G01N 15/0826; G01N 33/24; G01N 2203/0067; F42B 35/00; E21B 43/117; E21B 2200/20
See application file for complete search history.

(56) References Cited

U.S. PATENT DOCUMENTS

| | | | |
|---|---|---|---|
| 2009/0217739 A1* | 9/2009 | Hardesty | F42B 35/00 73/35.17 |
| 2010/0133005 A1* | 6/2010 | Bell | E21B 21/085 175/2 |

(Continued)

FOREIGN PATENT DOCUMENTS

| | | | | |
|---|---|---|---|---|
| EP | 2932185 B1 * | 5/2018 | | E21B 43/116 |
| WO | 2016126396 A1 | 8/2016 | | |
| WO | 2018132105 A1 | 7/2018 | | |

OTHER PUBLICATIONS

PCT Application Serial No. PCT/US2018/062630, International Search Report, dated Aug. 22, 2019, 3 pages.

(Continued)

*Primary Examiner* — Natalie Huls
(74) *Attorney, Agent, or Firm* — Delizio, Peacock, Lewin & Guerra (57) ABSTRACT

A method includes determining a perforation tunnel geometry of a perforation tunnel in a solid sample, the perforation tunnel created by activating a shaped charge in proximity to the solid sample. The method also includes performing a first flow test on the solid sample and creating an analog aperture having an aperture geometry in a solid sample analog of the solid sample, wherein the aperture geometry and the perforation tunnel geometry satisfies a similarity threshold. The method also includes performing a second flow test on the solid sample analog and determining a shaped charge effect based on a comparison between a second flow test result and a first flow test result.

20 Claims, 5 Drawing Sheets

(51) Int. Cl.
*G01N 15/08* (2006.01)
*E21B 43/117* (2006.01)
*G01N 33/24* (2006.01)
*F42B 35/00* (2006.01)
*F42B 1/028* (2006.01)

(52) U.S. Cl.
CPC ........ *G01N 15/0826* (2013.01); *E21B 43/117* (2013.01); *E21B 2200/20* (2020.05); *F42B 1/028* (2013.01); *G01N 33/24* (2013.01); *G01N 2203/0067* (2013.01)

(56) References Cited

U.S. PATENT DOCUMENTS

| | | | | |
|---|---|---|---|---|
| 2011/0017447 | A1* | 1/2011 | Zaleski, Jr. | G01N 23/046 166/250.01 |
| 2012/0233095 | A1 | 9/2012 | Evensen | |
| 2014/0366620 | A1* | 12/2014 | Haggerty | G01N 15/082 73/152.02 |
| 2015/0346119 | A1* | 12/2015 | Haggerty | E21B 49/00 378/4 |
| 2019/0011422 | A1* | 1/2019 | McGregor | E21B 43/11 |

OTHER PUBLICATIONS

PCT Application Serial No. PCT/US2018/062630, International Written Opinion, dated Aug. 22, 2019, 7 pages.

\* cited by examiner

SHAPED CHARGE EFFECT MEASUREMENT

BACKGROUND

The disclosure generally relates to the field of material testing and more particularly to flow property measurements.

A shaped charge is an explosive device designed to perforate rock and produce tunnels having a specified geometry in rock. Once positioned and activated next to rock, the shaped charge explodes and liner inside of the shaped charge is propelled into the rock. In addition, the shaped charge explosion generates a set of fractures having a fracture pattern. The liner perforates the rock and generates one or more perforation tunnels. These perforation tunnels increase the conduit of flow between a wellbore and hydrocarbon sources that are in the rock or connected to the rock. The effect that the set of fractures has on the permeability depends in part on the fracture pattern.

A shaped charge design can be characterized by various parameters, such as charge geometry, liner type, liner geometry, etc. Changes in shaped charge design result in subsequent changes in tunnel geometry and fracture patterns. Because of the relationship between rock permeability, tunnel geometry, and fracture patterns, increasing the understanding of the relationship between shaped charges and their corresponding effects on material permeability allows increased production of hydrocarbons. Operational maneuvers such as free gun volume control and wellbore underbalancing also factor into the resulting permeability of the perforation tunnel.

BRIEF DESCRIPTION OF THE DRAWINGS

Embodiments of the application can be better understood by referencing the accompanying drawings.

DESCRIPTION OF EMBODIMENTS

The description that follows includes example systems, methods, techniques, and program flows that embody embodiments of the disclosure. However, it is understood that this disclosure can be practiced without these specific details. For instance, this disclosure refers to using a computerized tomography (CT) scan. Aspects of this disclosure can instead be applied to other imaging methods such as magnetic resonance imaging. In other instances, well-known instruction instances, protocols, structures and techniques have not been shown in detail in order to avoid obfuscating the description.

Various embodiments relate to methods and related systems for determining a shaped charge effect after activation of a shaped charge. In some embodiments, a method includes activating a shaped charge in the proximity of a solid sample (e.g. a first rock sample) to create one or more perforation tunnels and a set of fractures. The method also includes performing a first flow test on the solid sample based on a pressure difference value, wherein performing the flow test can include performing a physical flow test or performing a computational flow simulation. In some embodiments, the pressure difference value can be within a pressure difference range corresponding to a target subsurface formation. The method can also include measuring the perforation tunnel to determine its tunnel geometry using methods such as performing CT scans of the interior.

The method can also include physically creating a new aperture in an analog of the solid sample that has an aperture geometry similar (i.e. sufficiently similar to satisfy a similarity threshold) to the tunnel geometry. The method can also include performing a second flow test on the solid sample analog that moves fluid through the analog aperture of the solid sample analog. The method can include comparing the results of the first flow test and the second flow test to determine one or more shaped charge effects on a property of the solid sample. The shaped charge effect can be binary/categorical, such as "increasing permeability" or "decreasing permeability." The shaped charge effect can also be quantitative and include both an expected property change along with a confidence interval for the expected property change. For example, the shaped charge effect can be a permeability increase of 100 millidarcy with a 90% confidence interval of 20 millidarcy in a solid sample.

By determining the shaped charge effect on fluid flow properties, the methods and related systems can provide a means of optimizing shaped charge selection and design. Optimized shaped charge selection and design can reduce perforation tunnel skin and increase productivity after perforation. In addition, optimized shaped charge selection and design can lower breakdown pressures and improve proppant displacement performance in a hydraulic fracturing process.

Example Core

Figure 1:
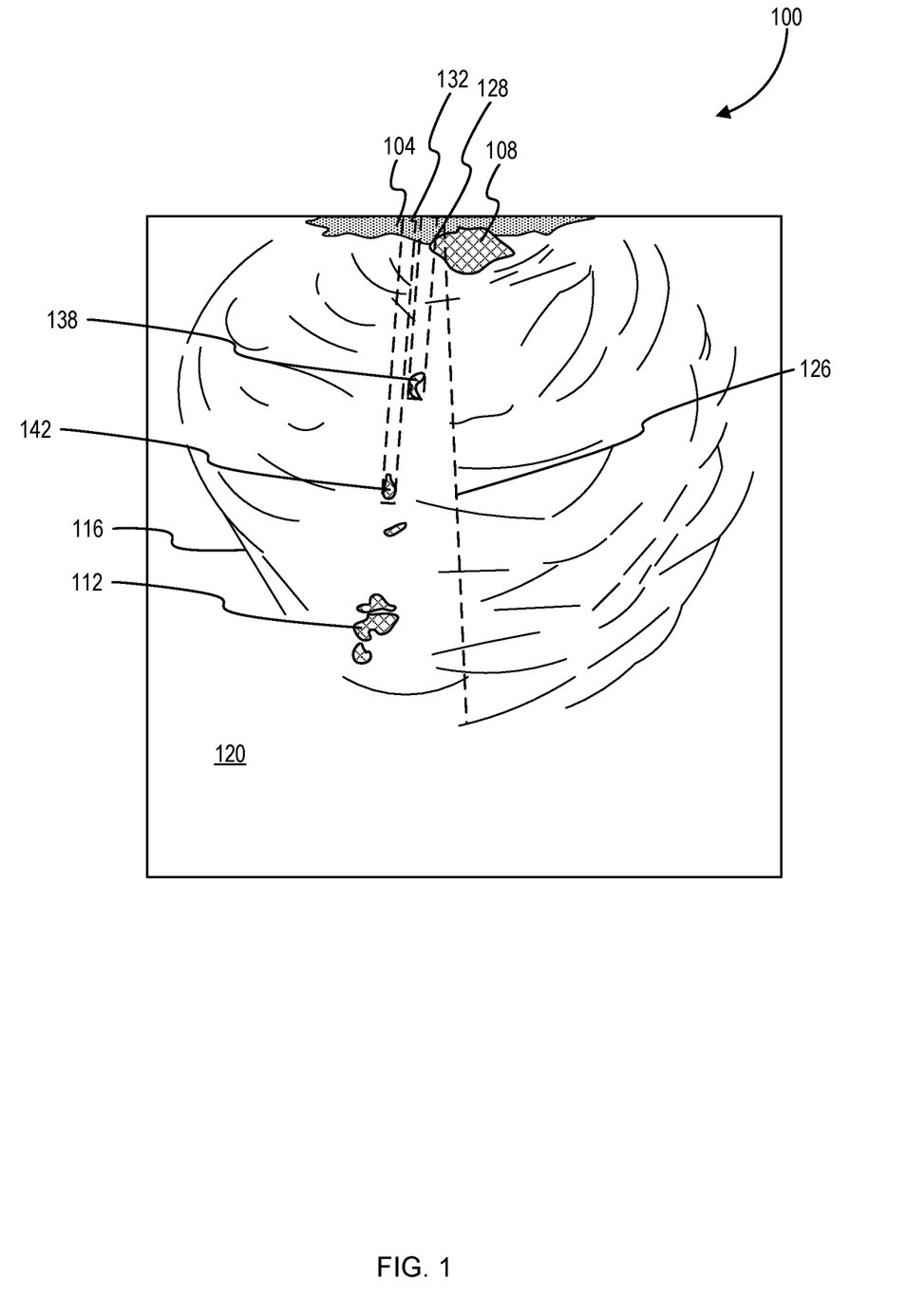
FIG. 1 depicts an idealized cross-sectional image a perforated rock sample using a shaped charge.

FIG. 1 depicts an idealized cross-sectional image a perforated rock sample using a shaped charge. The cross-sectional image 100 is an idealized diagram of a rock sample having a rock sample interior 120 perforated by a shaped charge. A shatter zone 104 shows the initial impacted zone created by the shaped charge. After a shaped charge is activated next to a rock sample, the liner can be broken up into multiple liner components that are jetted into the rock sample. Multiple liner components can perforate the rock sample with the liner components having paths that end at various distances from the initial impact zone. For example, some liner component paths can end close to the shatter zone 104, as shown by a first liner component 108. Alternatively, some liner component paths can end far from the initial impact zone, as shown in the second liner component 112. Each pellet of the liner components can form a perforation tunnel such as the perforation tunnel 128 created by the third liner component 138 or the perforation tunnel 132 created by the third liner component 142 that penetrates into the rock sample interior 120. The combined shape of the set of perforation tunnels created by the set of liner components can be described as having a tunnel geometry. In addition, the activation of the shaped charge can create a set of fractures 116 having a fracture pattern, wherein the fracture pattern is a semi-circular arrangement around the shatter zone 104 in the rock sample interior 120. As shown in this example, the fracture pattern has a fracture pattern radius 126, wherein the fracture pattern radius 126 represents a maximum distance that fractures exceeding a particular fracture length threshold is from the impact region.

In some embodiments, fluids can be passed through the rock sample interior 120 towards the shatter zone 104. A method can be used to analyze the fluids and quantify the effect that the set of fractures 116 have on the flow of the fluids by comparing the fluid flow measurements to an analog sample of the perforated rock sample. Using this comparison, a shaped charge effect can be determined. By examining multiple shaped charge effects and the shaped charge designs they each correspond with, the method can be used to optimize a shaped charge design.

Example Flowchart

Figure 2:
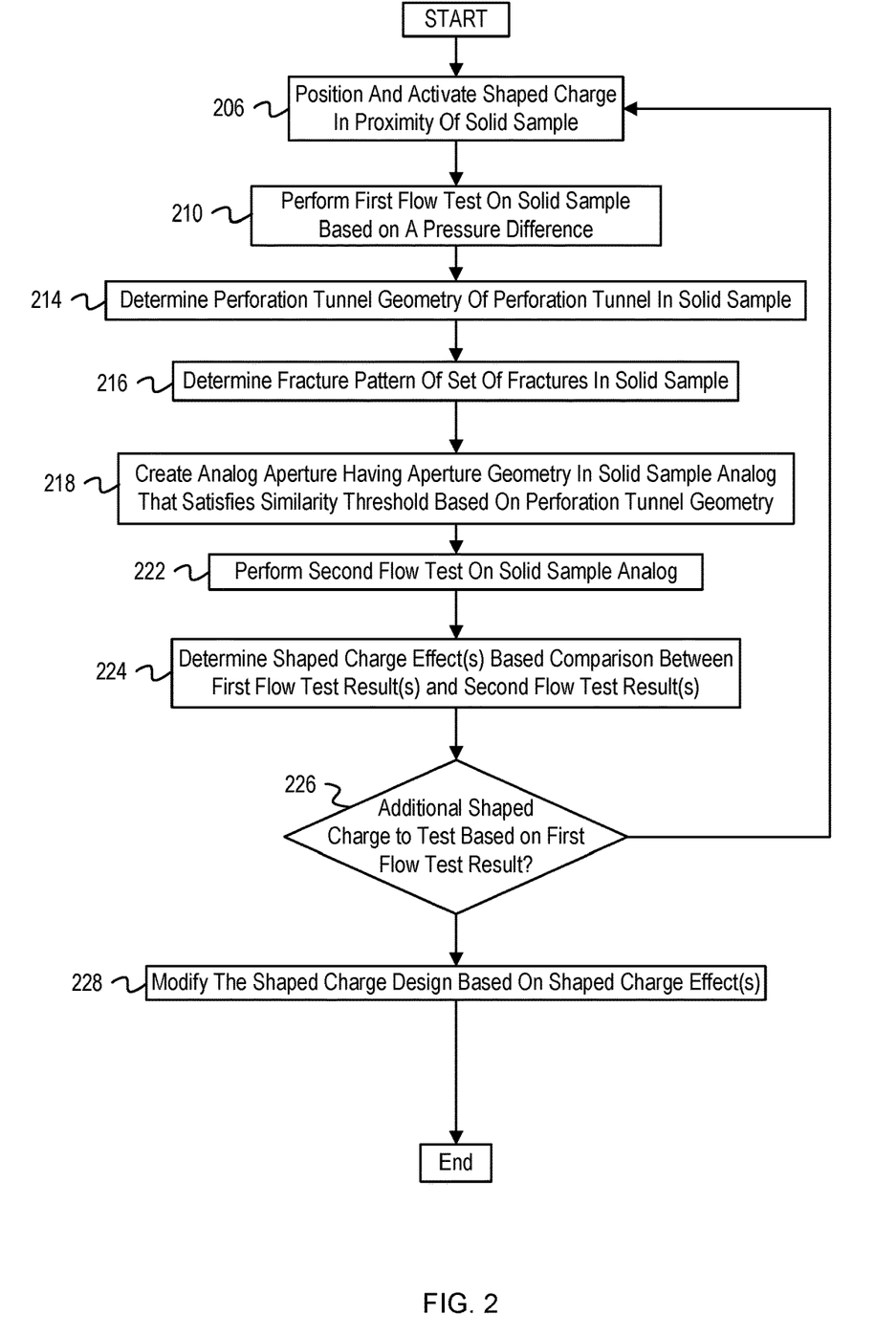
FIG. 2 depicts a flowchart of operations to determine a shaped charge effect.

FIG. 2 depicts a flowchart of operations to determine a shaped charge effect. FIG. 2 depicts a flowchart 200 of operations that are described with reference to a system comprising a processor. Operations of the flowchart 200 start at block 206.

At block 206, a shaped charge is positioned and activated in proximity of a solid sample. The shaped charges can be positioned manually or using an automated assembly controllable by the system. For example, the system can transmit program code instructions to a robotic assembly to attach the shaped charge to the solid sample. In some embodiments, the shaped charges can be positioned to be in contact with a solid sample such as a rock sample. Activating the shaped charge can occur by triggering an explosion of the shaped charge. The explosion of the shaped charge can generate a shockwave and force liner components inside of the shaped charge to perforate the solid sample and create a perforation tunnel as well as a set of fractures having a fracture geometry. The total volume encompassing the perforation tunnel and set of fractures can be described as an impact region of the solid sample. For example, with reference to FIG. 1, after activating a first shaped charge, the first shaped charge can generate a solid sample having a perforation tunnel and a set of fractures similar to that shown in the cross-sectional image 100.

At block 210, a first flow test can be performed on the solid sample based on a pressure difference value. The first flow test can be a reproduction of a flowback test in a formation. In some embodiments, the first flow test can be a physical flow test wherein a fluid exposed to one end of the solid sample can be pushed through the solid sample using a pressure difference at the pressure difference value. At least a measurable portion of the fluid flows through the set of fractures and/or the perforation tunnel(s). In some embodiments, the pressure difference value can be equal to a target pressure difference value in a pressure difference range of a particular formation, wherein the pressure difference range is a measured or calculated range of pressure difference values corresponding to the particular formation. For example, if a particular formation has a pressure difference range of 0-5000 pounds per square inch (psi), the pressure difference value used for the first flow test can be 4000 psi or some other pressure in the pressure difference range of 0-5000 psi. The fluids used during the flow test can include water, hydrocarbons, radioactive materials, polar fluids, nonpolar fluids, etc. In addition, the solid sample can have pre-existing fluids capable of escaping the solid sample through the impact region of the solid sample. For example, the solid sample can be a shale sample containing hydrocarbons that can escape through the impact region after application of a pressure difference on the solid sample. As fluid escapes through the solid sample, the system can measure the fluid flow, fluid properties, and pressure changes across the solid sample using one or more sensors that are communicable with the system.

In some embodiments, the flow test can be performed using a computational flow simulator instead of a physical flow test. For example, with reference to FIG. 1, a computational flow simulator can be used to perform a computational flow simulation using the pressure difference value to generate one or more flow test result(s). The computational flow simulation can be based on a digital model of the solid sample that includes the one or more tunnel geometries of the perforation tunnels and the fracture pattern of the set of fractures depicted in the cross-sectional image 100.

At block 214, a perforation tunnel geometry of a perforation tunnel in the solid sample is determined. The perforation tunnel of the solid sample is a physical aperture in the solid sample created by a liner component from the shaped charge after the shaped charge is activated. In some embodiments, the perforation tunnel geometry can be determined by using the system to perform and analyze one or more CT scans of the solid sample after shaped charge activation, wherein the CT scan (or set of CT scans) can provide a three-dimensional model of the perforation tunnel. For example, with reference to FIG. 1, the system can perform a CT scan of the solid sample to determine that the perforation tunnel 132 can have a perforation tunnel geometry with a length of 10 centimeter (cm), a radius of 0.50 cm at an end of the perforation tunnel geometry, and a cross-sectional area of 0.79 $cm^2$ at the same end of the perforation tunnel geometry.

At block 216, a fracture pattern of the set of fractures in the sold sample is determined. In some embodiments, the fracture pattern can be determined by using the system to measure the geometry of one or more fractures in the set of fractures. The fracture pattern and its set of corresponding fracture geometries can be measured by analyzing one or more CT scans of the solid sample after shaped charge activation. For example, with reference to FIG. 1, the set of fractures 116 can be measured to show a semi-circular fracture pattern, with a fracture pattern radius of 25 cm and individual fractures ranging between 0.0-4.0 cm in length.

At block 218, an analog aperture having an aperture geometry is created in a solid sample analog, wherein the aperture geometry satisfies a similarity threshold based on the perforation tunnel geometry. The solid sample analog is a solid material that matches at least one of a formation source, composition and material property of the solid sample. For example, the solid sample analog can be from the same formation as the solid sample (thus sharing a formation source). As a second example, the solid sample analog can be a manufactured material having the same density and elastic compression strength as the solid sample. The analog aperture can be created through various material-destruction methods including but not limited to drilling, laser-cutting, plasma cutting, sawing, etc. In general, creation of the aperture in the solid sample analog can be done without generating a fracture pattern similar to the fracture pattern of the set of fractures in the solid sample described for block 216 (e.g. having the same fracture pattern radius).

The similarity threshold based on the perforation tunnel geometry can be or include the criterion/criteria that one or more dimensional metrics (e.g. a length, cross-sectional area, volume, etc.) of the aperture geometry is within a predetermined range (e.g. a percentage, an absolute value, etc.) of its corresponding dimensional metric for the solid sample analog. For example, the similarity threshold can be that a cross-sectional area of an end of the aperture geometry is within 10% of a cross-sectional area of an end of the perforation tunnel geometry. As another example, the similarity threshold can include a criterion that an end-to-end length (either straight-line length or restricted to the perforation tunnel interior volume) of the aperture geometry is within 0.1 cm of a corresponding end-to-end length of the perforation tunnel geometry. As another example, the similarity threshold can include a criterion that a total volume of the aperture geometry is within 5.0% of the total volume of the perforation tunnel geometry. In some embodiments, other similarity threshold values and types can be used and that such values and types are within the scope of the inventive subject matter.

At block 222, a second flow test is performed on the solid sample analog. The second flow test can have the same testing parameters as the first flow test performed at block 210 above. For example, both the first flow test and the second flow test can be lab flow back tests that move fluid through their respective test materials (i.e. either the solid sample or solid sample analog) using the same pressure difference value. Alternatively, the second flow test can have different testing parameters than the first flow test. For example, the second flow test can use a second pressure difference value that is different from the pressure difference value used during the first flow test to provide results for determining shaped charge effects at the second pressure difference value.

In some embodiments, the second flow test can include using the computational flow simulator described above to determine one or more second flow test results instead of or in addition to performing a physical flow test. For example, a system can use a computational flow simulator to perform a computational flow simulation using the same pressure difference value as described above for block 210 to generate one or more second flow test results. The computational flow simulation can be based on a digital model of the solid sample analog that includes the one or more aperture geometries of the analog apertures.

At block 224, one or more shaped charge effects of the fracture pattern are determined based on a comparison of one or more first flow test results and one or more second flow test results. The comparison can be determined using a computational simulation, statistical calculation, or other comparison method. The comparison can include determining the value of a difference between the fluid flow of the first solid sample and the fluid flow of the second solid sample, between the calculated permeability value of the first solid sample and calculated permeability value of the second solid sample, between the flow rate of the first solid sample and the flow rate of the second solid sample, etc. By correlating the difference with the fracture pattern and/or its corresponding shaped charge, the system can determine a shaped charge effect corresponding to the shaped charge.

At block 226, a determination is made if whether an additional shaped charge should be tested based on the first flow test result. An additional shaped charge can be tested based on whether a shaped charge effect threshold is satisfied by a shaped charge effect, wherein the shaped charge effect itself is based on the first flow test result. For example, the shaped charge effect threshold can be a permeability change threshold and an additional shaped charge should be tested if the measured permeability change of the solid sample is less than the permeability change threshold. In embodiments wherein multiple shaped charges sharing the same shaped charge design are used for multiple iterations of the flow testing operations from blocks 206-226 described above, the quantification of the shaped charge effect can made more accurate by results from previous iterations. If the additional shaped charge should be tested based on the first flow test result, the operations can return to block 202. Otherwise, the operations proceed to block 228.

At block 228, the shaped charge design is modified based on the one or more shaped charge effects. In some embodiments, the system can have a target effect threshold and modify a shaped charge design to satisfy the target effect threshold. For example, the system can have a target effect threshold of at least a permeability increase of 2.0 millidarcy and increase the free gun volume of the shaped charge design in response to the determination that a shaped charge having the shaped charge design does not increase solid sample permeability by at least 2.0 millidarcy. Once the shaped charge design is modified, a new shaped charge having the modified shaped charge design can be used in a downhole environment and activated to perforate a well. In addition, the shaped charge effects determined and collected using the operations described above can be collected into a shaped charge dataset that correlates shaped charge effects, fracture pattern (or characteristics thereof), and/or their corresponding shaped charges. This shaped charge dataset can then be used to select an optimal shaped charge.

Figure 3:
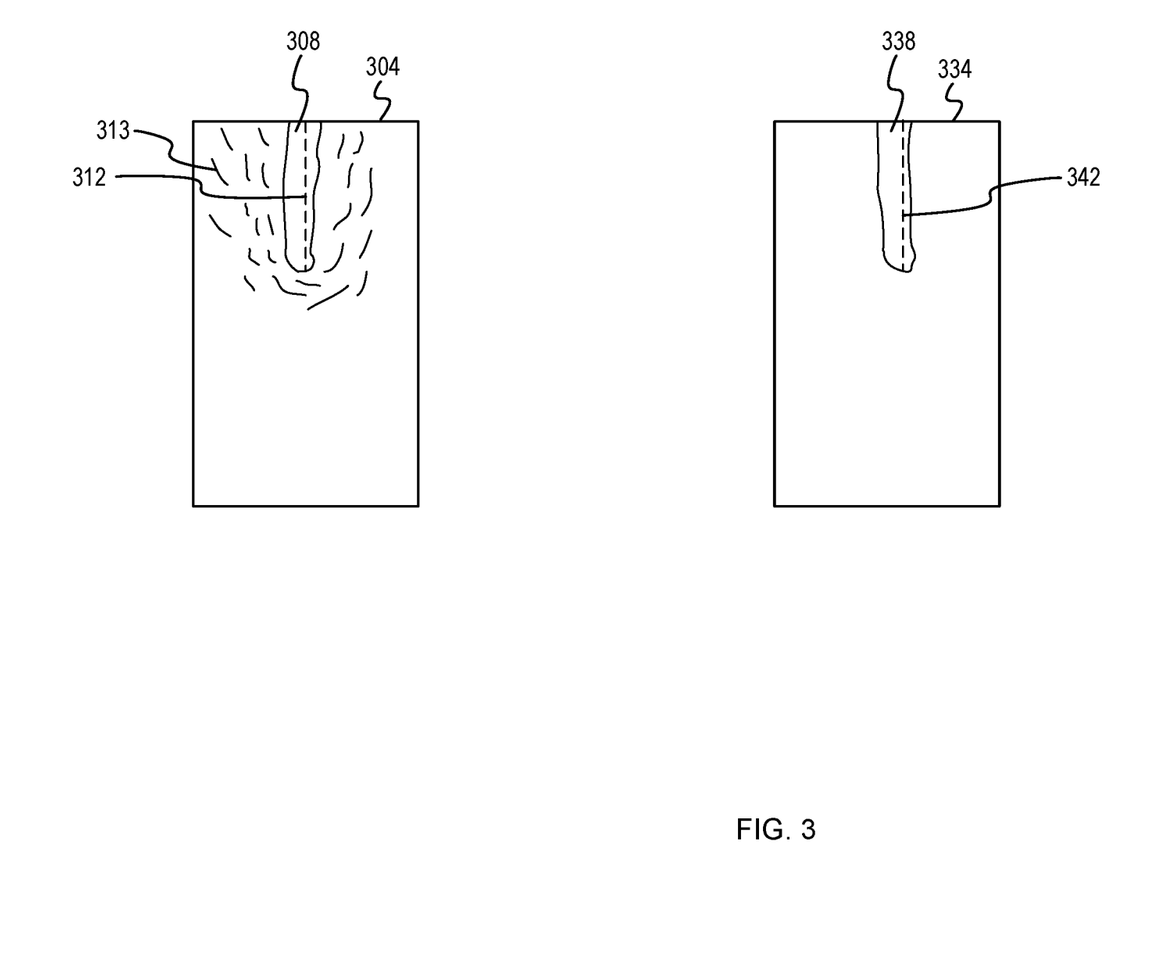
FIG. 3 depicts a comparison of a perforation tunnel in a solid sample and an analog aperture in a solid sample analog.

FIG. 3 depicts a comparison of a perforation tunnel in a solid sample and an analog aperture in a solid sample analog. A solid sample 304 includes a perforation tunnel 308 and multiple fractures such as the fracture 313. A system can determine the perforation tunnel geometry of the perforation tunnel 308 using a CT scan and determine that the tunnel length 312 of the perforation tunnel 308 is 3.0 inches. After performing the CT scan, the system can perform a first flow test on the perforation tunnel 308 by using a pressure difference value to move fluid through the solid sample 304, wherein at least a portion of the fluid flows through the perforation tunnel 308 and the fracture 313.

A solid sample analog 334 is shown to the right of the solid sample 304. The solid sample analog 334 can be from the same formation source as the solid sample 304 or can share a same material property such as compressive strength or fracture strength as the solid sample 304. An analog aperture 338 can be drilled into the solid sample analog 334, wherein the aperture length 342 of the analog aperture 338 is equal to the tunnel length 312. In addition, a second flow test on the analog aperture 338 can be performed by using the same pressure difference value used above in the first flow test to move fluid through the solid sample 304, wherein at least a portion of the fluid approaches the analog aperture 338. The system can then compare the first flow test results and the second flow test results to determine shaped charge effects such as differences in flow rate, changes in effective sample permeability, etc.

Example Subsurface Perforation System

Figure 4:
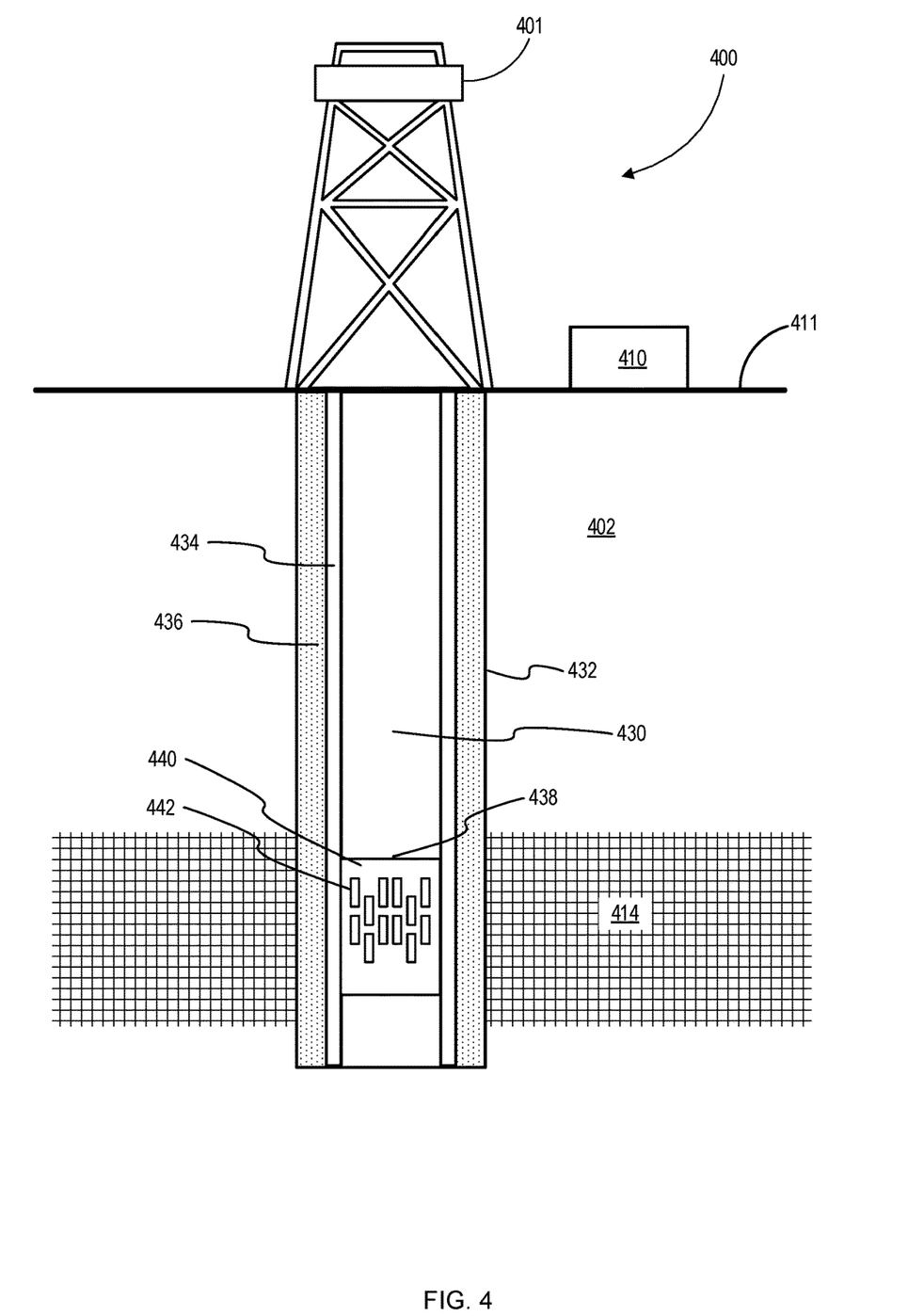
FIG. 4 depicts an example subsurface perforation system.

FIG. 4 depicts an example subsurface perforation system. Referring to FIG. 4, a subsurface perforation system 400 operating from an onshore oil and gas platform is illustrated. A platform 401 is centered over an oil and gas formation 414 located within the subsurface 402. A wellbore 432 extends through the various earth strata including the oil and gas formation 414. A casing 434 is cemented within wellbore 432 by cement 436. Work string 430 include various tools including shaped charge apparatus 438. When it is desired to perforate the oil and gas formation 414, the work string 430 is lowered through casing 434 until the shaped charge apparatus 438 is positioned adjacent to the oil and gas formation 414. Thereafter, the shaped charge apparatus 438 is fired by detonating the shaped charges that are disposed within charge carrier 440 and aligned with recesses 442 of charge carrier 440. Upon detonation, the liners of the shaped charges form jets that pass through recesses 442 of charge carrier 440 and form a spaced series of perforation tunnels extending outwardly through casing 434, cement 436 and into the oil and gas formation 414. A surface system 410 on the surface 411 can include a processor and can have a non-transitory machine-readable medium storing program code to lower the charge carrier 440. One or more of the shaped charges aligned with the recesses 442 can be selected using a shaped charge dataset including the values of the shaped charge effects determined from the operations described above for FIG. 2.

Even though FIG. 4 depicts a vertical well, it should be noted that the shaped charge apparatus 438 described above is equally well-suited for use in deviated wells, inclined wells or horizontal wells. Also, even though FIG. 1 depicts an onshore operation, it should be noted that the shaped charge apparatus 438 apparatus of the present invention is equally well-suited for use in offshore operations.

Example Computer Device

Figure 5:
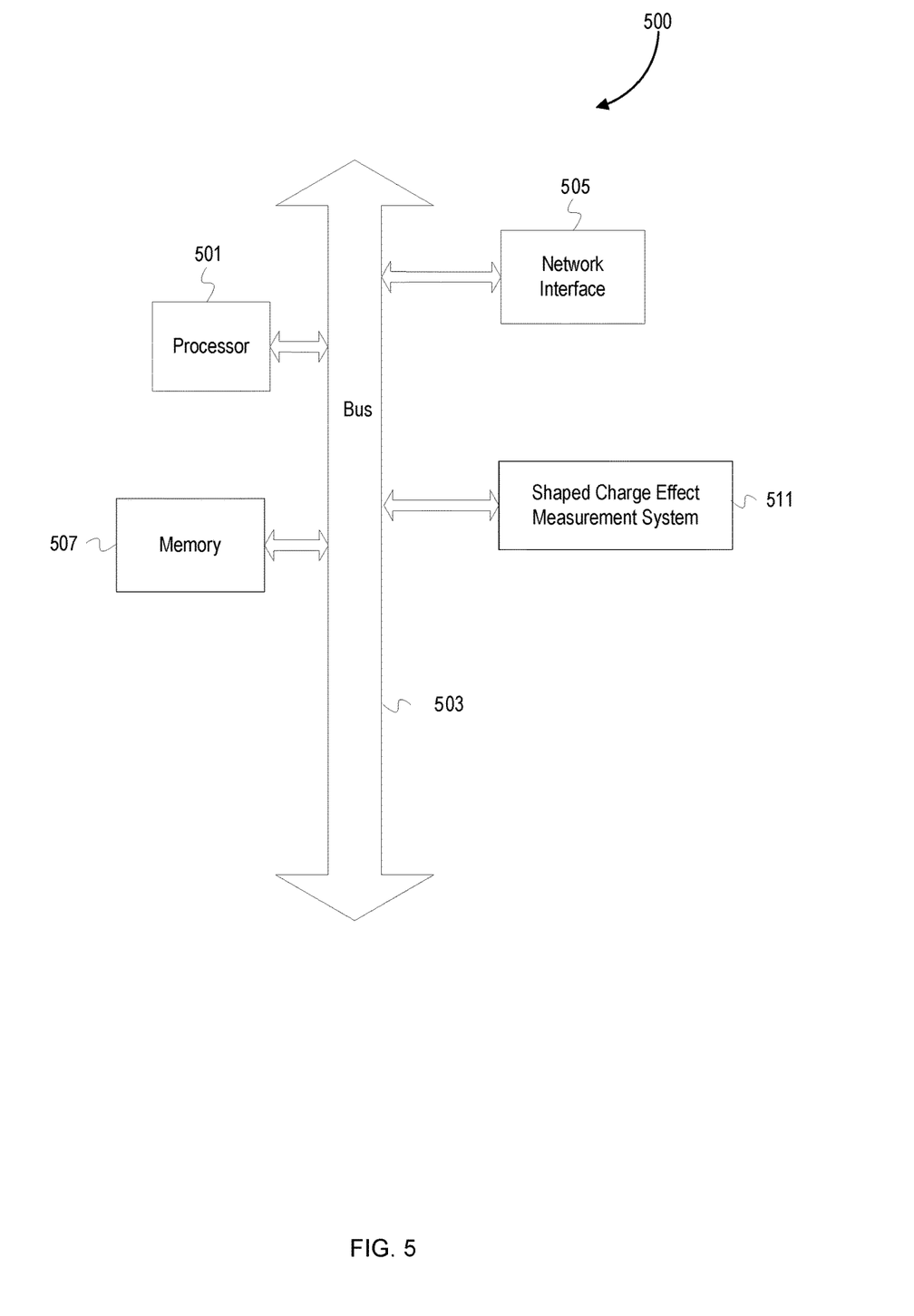
FIG. 5 depicts an example computer device.

FIG. 5 depicts an example computer device. A computer device 500 includes a processor 501 (possibly including multiple processors, multiple cores, multiple nodes, and/or implementing multi-threading, etc.). The computer device 500 includes a memory 507. The memory 507 can be system memory (e.g., one or more of cache, SRAM, DRAM, zero capacitor RAM, Twin Transistor RAM, eDRAM, EDO RAM, DDR RAM, EEPROM, NRAM, RRAM, SONOS, PRAM, etc.) or any one or more of the above already described possible realizations of machine-readable media. The memory 507 can be used as a buffer. The computer device 500 also includes a bus 503 (e.g., PCI, ISA, PCI-Express, HyperTransport® bus, InfiniBand® bus, NuBus, etc.) and a network interface 505 (e.g., a Fiber Channel interface, an Ethernet interface, an internet small computer system interface, SONET interface, wireless interface, etc.).

In some embodiments, the computer device 500 includes a shaped charge effect measurement system 511. With respect to FIG. 2, the shaped charge effect measurement system 511 can perform one or more the operations described above in the flowchart 200. For example, the shaped charge effect measurement system 511 can determine a perforation tunnel geometry and determine a shaped charge effect based on a comparison between a first flow test result and a second flow test result. Any one of the previously described functionalities can be partially (or entirely) implemented in hardware and/or on the processor 501. For example, the functionality can be implemented with an application specific integrated circuit, in logic implemented in the processor 501, in a co-processor on a peripheral device or card, etc. Further, realizations can include fewer or additional components not illustrated in FIG. 5 (e.g., video cards, audio cards, additional network interfaces, peripheral devices, etc.). The processor 501 and the network interface 505 are coupled to the bus 503. Although illustrated as being coupled to the bus 503, the memory 507 can be coupled to the processor 501. The computer device 500 can be integrated into component(s) of a pipe downhole and/or be a separate device at the surface that is communicatively coupled to the BHA downhole for controlling and processing signals (as described herein).

As will be appreciated, aspects of the disclosure can be embodied as a system, method or program code/instructions stored in one or more machine-readable media. Accordingly, aspects can take the form of hardware, software (including firmware, resident software, micro-code, etc.), or a combination of software and hardware aspects that can all generally be referred to herein as a "circuit," "module" or "system." The functionality presented as individual modules/units in the example illustrations can be organized differently in accordance with any one of platform (operating system and/or hardware), application ecosystem, interfaces, programmer preferences, programming language, administrator preferences, etc.

Any combination of one or more machine-readable medium(s) can be utilized. The machine-readable medium can be a machine-readable signal medium or a machine-readable storage medium. A machine-readable storage medium can be, for example, but not limited to, a system, apparatus, or device, that employs any one of or combination of electronic, magnetic, optical, electromagnetic, infrared, or semiconductor technology to store program code. More specific examples (a non-exhaustive list) of the machine-readable storage medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a machine-readable storage medium can be any tangible medium that can contain, or store a program for use by or in connection with an instruction execution system, apparatus, or device. A machine-readable storage medium is not a machine-readable signal medium.

A machine-readable signal medium can include a propagated data signal with machine readable program code embodied therein, for example, in baseband or as part of a carrier wave. Such a propagated signal can take any of a variety of forms, including, but not limited to, electromagnetic, optical, or any suitable combination thereof. A machine-readable signal medium can be any machine readable medium that is not a machine-readable storage medium and that can communicate, propagate, or transport a program for use by or in connection with an instruction execution system, apparatus, or device.

Program code embodied on a machine-readable medium can be transmitted using any appropriate medium, including but not limited to wireless, wireline, optical fiber cable, RF, etc., or any suitable combination of the foregoing.

Computer program code for carrying out operations for aspects of the disclosure can be written in any combination of one or more programming languages, including an object oriented programming language such as the Java® programming language, C++ or the like; a dynamic programming language such as Python; a scripting language such as Perl programming language or PowerShell script language; and conventional procedural programming languages, such as the "C" programming language or similar programming languages. The program code can execute entirely on a stand-alone machine, can execute in a distributed manner across multiple machines, and can execute on one machine while providing results and or accepting input on another machine.

The program code/instructions can also be stored in a machine-readable medium that can direct a machine to function in a particular manner, such that the instructions stored in the machine-readable medium produce an article of manufacture including instructions which implement the function/act specified in the flowchart and/or block diagram block or blocks.

Additional Terminology and Variations

Use of the phrase "at least one of" preceding a list with the conjunction "and" should not be treated as an exclusive list and should not be construed as a list of categories with one item from each category, unless specifically stated otherwise. A clause that recites "at least one of A, B, and C" can be infringed with only one of the listed items, multiple of the listed items, and one or more of the items in the list and another item not listed. Use of the term "set" can be treated as meaning "group having at least one of" For example, "set of items" can be treated as meaning "group of items having at least one item." As used in this application, a first material shares a material property with a second material when both the first material and the second material have corresponding material property values that are no greater than 10% different from each other. For example, a first rock shares a compressive strength with a second rock if the first rock is 30 Megapascals and the second rock is 29 Megapascals. As used in this application, a first material shares a composition with a second material when both the first material and the second material have corresponding compositions wherein the constituent minerals (e.g. quartz, perovskite, etc.) that are greater than 10% in the composition of either materials are similar (within 10%) of each other. For example, a first rock composed of 70% quartz, 20% perovskite, and 5% sphalerite shares a composition with a second rock composed of 69% quartz, 21% perovskite and 5% cuprite.

Example Embodiments

Example embodiments include the following:

Embodiment 1: A method comprising: determining a perforation tunnel geometry of a perforation tunnel in a solid sample, the perforation tunnel created by activating a shaped charge in proximity to the solid sample; performing a first flow test on the solid sample; creating an analog aperture having an aperture geometry in a solid sample analog, wherein the aperture geometry and the perforation tunnel geometry satisfies a similarity threshold, and wherein the solid sample analog shares at least one of a material property, composition and source formation with the solid sample; performing a second flow test on the solid sample analog; and determining a shaped charge effect based on a comparison between a second flow test result and a first flow test result.

Embodiment 2: The method of Embodiment 1, wherein the similarity threshold is based on at least one of a volume of the perforation tunnel geometry, a cross-sectional area of the perforation tunnel geometry and a length of the perforation tunnel geometry.

Embodiment 3: The method of Embodiments 1 or 2, wherein determining the perforation tunnel geometry comprises using a computerized tomography scan to generate a three-dimensional model of the perforation tunnel.

Embodiment 4: The method of any of Embodiments 1-3, wherein the first flow test is a physical flow test, and wherein a first fluid of the first flow test comes in contact with the perforation tunnel.

Embodiment 5: The method of any of Embodiments 1-4, further comprising determining a fracture pattern of a set of fractures in the solid sample created by activation of the shaped charge.

Embodiment 6: The method of any of Embodiments 1-5, wherein the shaped charge effect is at least one of a permeability change, a flow rate change and a perforation tunnel skin change.

Embodiment 7: The method of any of Embodiments 1-6, further comprising modifying a free gun volume of a shaped charge design of the shaped charge based on the shaped charge effect.

Embodiment 8: The method of any of Embodiments 1-7, further comprising determining a target pressure difference value within a pressure difference range of a target subsurface formation, wherein performance of the second flow test is based on the target pressure difference value.

Embodiment 9: A method comprising: determining a perforation tunnel geometry of a perforation tunnel in a solid sample, the perforation tunnel created by activating a shaped charge in proximity to the solid sample; performing a first flow test on the solid sample based on a target pressure difference value; performing a second flow test on a solid sample analog, wherein an analog aperture is in the solid sample analog and has an aperture geometry, wherein the aperture geometry and the perforation tunnel geometry satisfies a similarity threshold, and wherein the solid sample analog shares at least one of a material property, composition and source formation with the solid sample; and determining a shaped charge effect of the shaped charge based on a comparison between a second flow test result and a first flow test result.

Embodiment 10: The method of Embodiment 9, wherein the first flow test is a physical flow test, and wherein a first fluid of the first flow test comes in contact with the perforation tunnel, and wherein the first flow test includes applying a pressure difference at the target pressure difference value.

Embodiment 11: The method of Embodiments 9 or 10, wherein the similarity threshold is based on at least one of a volume of the perforation tunnel geometry, a cross-sectional area of the perforation tunnel geometry and a length of the perforation tunnel geometry.

Embodiment 12: The method of any of Embodiments 9-11, wherein determining the perforation tunnel geometry comprises using a computerized tomography scan to generate a three-dimensional model of the perforation tunnel.

Embodiment 13: The method of any of Embodiments 9-12, further comprising determining a fracture geometry of a set of fractures in the solid sample.

Embodiment 14: The method of any of Embodiments 9-13, wherein the shaped charge effect is at least one of a permeability change, a flow rate change and a perforation tunnel skin change.

Embodiment 15: One or more non-transitory machine-readable media comprising program code for determining a shaped charge effect, the program code to: determine a perforation tunnel geometry of a perforation tunnel and a fracture pattern of a set of fractures, wherein the perforation tunnel and the set of fractures are in a solid sample; perform a first flow test on the solid sample; perform a second flow test on a solid sample analog, wherein an analog aperture is in the solid sample analog and has an aperture geometry, wherein the aperture geometry and the perforation tunnel geometry satisfies a similarity threshold, and wherein the solid sample analog shares at least one of a material property, composition and source formation with the solid sample; and determine the shaped charge effect based on a comparison between a second flow test result and a first flow test result.

Embodiment 16: The one or more non-transitory machine-readable media of Embodiment 15, wherein the similarity threshold is based on at least one of a volume of the perforation tunnel geometry, a cross-sectional area of the perforation tunnel geometry and a length of the perforation tunnel geometry.

Embodiment 17: The one or more non-transitory machine-readable media of Embodiments 15 or 16, wherein the program code to determine the perforation tunnel geometry comprises program code to use a computerized tomography scan to generate a three-dimensional model of the perforation tunnel.

Embodiment 18: The one or more non-transitory machine-readable media of any of Embodiments 15-17, wherein the shaped charge effect is at least one of a permeability change, a flow rate change and a perforation tunnel skin change.

Embodiment 19: The one or more non-transitory machine-readable media of any of Embodiments 15-18, further comprising program code to determine the fracture pattern of the set of fractures in the solid sample.

Embodiment 20: The one or more non-transitory machine-readable media of any of Embodiments 15-19, wherein the program code to perform the first flow test comprises program code to perform a computational flow simulation based on a digital model comprising the perforation tunnel geometry and the fracture pattern.

What is claimed is:

1. A method comprising:
   determining a perforation tunnel geometry of a perforation tunnel in a solid sample, the perforation tunnel created by activating a shaped charge in proximity to the solid sample and including a set of fractures generated by the activation of the shaped charge, the set of fractures in proximity to the perforation tunnel geometry of the solid sample;
   performing a first flow test on the solid sample;
   creating an analog aperture having an aperture geometry in a solid sample analog, wherein the analog aperture is created using a method that does not result in forming a fracture pattern around the aperture geometry of the analog aperture, wherein the aperture geometry and the perforation tunnel geometry satisfies a similarity threshold, and wherein the solid sample analog shares at least one of a material property, composition and source formation with the solid sample;
   performing a second flow test on the solid sample analog; and
   determining a shaped charge effect based on a comparison between a second flow test result and a first flow test result.

2. The method of claim 1, wherein the similarity threshold is based on at least one of a volume of the perforation tunnel geometry, a cross-sectional area of the perforation tunnel geometry and a length of the perforation tunnel geometry.

3. The method of claim 1, wherein determining the perforation tunnel geometry comprises using a computerized tomography scan to generate a three-dimensional model of the perforation tunnel.

4. The method of claim 1, wherein the first flow test is a physical flow test, and wherein a first fluid of the first flow test comes in contact with the perforation tunnel.

5. The method of claim 1, further comprising determining a solid sample fracture pattern of the set of fractures in the solid sample created by activation of the shaped charge.

6. The method of claim 1, wherein the shaped charge effect is at least one of a permeability change, a flow rate change and a perforation tunnel skin change.

7. The method of claim 1, further comprising modifying a free gun volume of a shaped charge design of the shaped charge based on the shaped charge effect.

8. The method of claim 1, further comprising determining a target pressure difference value within a pressure difference range of a target subsurface formation, wherein performance of the second flow test is based on the target pressure difference value.

9. A method comprising:
   determining a perforation tunnel geometry of a perforation tunnel in a solid sample, the perforation tunnel created by activating a shaped charge in proximity to the solid sample and including a set of fractures generated by the activation of the shaped charge, the set of fractures in proximity to the perforation tunnel of the solid sample;
   performing a first flow test on the solid sample based on a target pressure difference value;
   performing a second flow test on a solid sample analog, wherein an analog aperture is in the solid sample analog and has an aperture geometry, wherein the analog aperture is created using a method that does not result in forming a fracture pattern around the aperture geometry of the analog aperture, and wherein the aperture geometry and the perforation tunnel geometry satisfies a similarity threshold, and wherein the solid sample analog shares at least one of a material property, composition and source formation with the solid sample; and
   determining a shaped charge effect of the shaped charge based on a comparison between a second flow test result and a first flow test result.

10. The method of claim 9, wherein the first flow test is a physical flow test, and wherein a first fluid of the first flow test comes in contact with the perforation tunnel, and wherein the first flow test includes applying a pressure difference at the target pressure difference value.

11. The method of claim 9, wherein the similarity threshold is based on at least one of a volume of the perforation tunnel geometry, a cross-sectional area of the perforation tunnel geometry and a length of the perforation tunnel geometry.

12. The method of claim 9, wherein determining the perforation tunnel geometry comprises using a computerized tomography scan to generate a three-dimensional model of the perforation tunnel.

13. The method of claim 9, further comprising determining a solid sample fracture geometry of the set of fractures in the solid sample.

14. The method of claim 9, wherein the shaped charge effect is at least one of a permeability change, a flow rate change and a perforation tunnel skin change.

15. One or more non-transitory machine-readable media comprising program code for determining a shaped charge effect, the program code to:
   determine a perforation tunnel geometry of a perforation tunnel and a fracture pattern of a set of fractures, wherein the perforation tunnel and the set of fractures are in a solid sample and formed by an activation of a shaped charge in proximity to the solid sample;
   perform a first flow test on the solid sample;
   perform a second flow test on a solid sample analog, wherein an analog aperture is in the solid sample analog and has an aperture geometry, wherein the analog aperture is created using a method that does not result in formation of one or more fractures around the aperture geometry of the analog aperture, and wherein the aperture geometry and the perforation tunnel geometry satisfies a similarity threshold, and wherein the solid sample analog shares at least one of a material property, composition and source formation with the solid sample; and determine the shaped charge effect based on a comparison between a second flow test result and a first flow test result.

16. The one or more non-transitory machine-readable media of claim 15, wherein the similarity threshold is based on at least one of a volume of the perforation tunnel geometry, a cross-sectional area of the perforation tunnel geometry and a length of the perforation tunnel geometry.

17. The one or more non-transitory machine-readable media of claim 15, wherein the program code to determine the perforation tunnel geometry comprises program code to use a computerized tomography scan to generate a three-dimensional model of the perforation tunnel.

18. The one or more non-transitory machine-readable media of claim 15, wherein the shaped charge effect is at least one of a permeability change, a flow rate change and a perforation tunnel skin change.

19. The one or more non-transitory machine-readable media of claim 15, further comprising program code to determine the fracture pattern of the set of fractures in the solid sample.

20. The one or more non-transitory machine-readable media of claim 19, wherein the program code to perform the first flow test comprises program code to perform a computational flow simulation based on a digital model comprising the perforation tunnel geometry and the fracture pattern.

* * * * *